(12) United States Patent
Yoo et al.

(10) Patent No.: US 11,443,118 B2
(45) Date of Patent: Sep. 13, 2022

(54) WORD EMBEDDING METHOD AND APPARATUS, AND WORD SEARCH METHOD

(71) Applicant: Samsung Electronics Co., Ltd., Suwon-si (KR)

(72) Inventors: Sanghyun Yoo, Seoul (KR); Young-Seok Kim, Suwon-si (KR); Junhwi Choi, Seongnam-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 261 days.

(21) Appl. No.: 16/822,436

(22) Filed: Mar. 18, 2020

(65) Prior Publication Data
US 2021/0110116 A1 Apr. 15, 2021

(30) Foreign Application Priority Data
Oct. 14, 2019 (KR) .......................... 10-2019-0127032

(51) Int. Cl.
*G06F 40/30* (2020.01)
*G06N 20/00* (2019.01)

(52) U.S. Cl.
CPC ............. *G06F 40/30* (2020.01); *G06N 20/00* (2019.01)

(58) Field of Classification Search
None
See application file for complete search history.

(56) References Cited

U.S. PATENT DOCUMENTS

| 2018/0253426 A1 | 9/2018 | Oh et al. |
| 2018/0336181 A1 | 11/2018 | Fink et al. |
| 2020/0311352 A1* | 10/2020 | Miura .................... G06N 3/049 |

FOREIGN PATENT DOCUMENTS

| JP | 2015-232894 A | 12/2015 |
| KR | 10-1797365 B1 | 11/2017 |

OTHER PUBLICATIONS

Tshitoyan et al., "Unsupervised word embeddings capture latent knowledge from materials science literature", Jul. 3, 2019, (Year: 2019).*
Mikolov, Tomas, et al., "Efficient Estimation of Word Representations in Vector Space." arXiv preprint arXiv:1301.3781, Sep. 7, 2013 (pp. 1-12).
Tshitoyan, Vahe, et al., "Unsupervised Word Embeddings Capture Latent Knowledge from Materials Science Literature," Nature, 571, 7763, 2019 (pp. 95-98).
Extended European Search Report dated Jan. 26, 2021 in counterpart European Application No. 20183255.7 (6 pages in English).
Eltyeb, Safaa et al., "Chemical named entities recognition: a review on approaches and applications", Journal of Cheminformatics, vol. 6, Issue 1, 2014 (pp. 1-12).

(Continued)

*Primary Examiner* — Nafiz E Hoque
(74) *Attorney, Agent, or Firm* — NSIP Law (57) ABSTRACT

A word embedding method and apparatus and a word search method are provided, wherein the word embedding method includes training a word embedding model based on characteristic information of a chemical substance, and acquiring an embedding vector of a word representing the chemical substance from the word embedding model, wherein the word embedding model is configured to predict a context word of an input word.

17 Claims, 8 Drawing Sheets

(56) References Cited

OTHER PUBLICATIONS

Krallinger, Martin et al., "CHEMDNER: The drugs and chemical names extraction challenge", *Journal of cheminformatics*, vol. 7, Issue 1, 2015 (pp. 1-11).
Tshitoyan, Vahe et al., "Unsupervised word embeddings capture latent knowledge from materials science literature", *Nature*, Jul. 19, 2019 (pp. 1-12).

* cited by examiner

WORD EMBEDDING METHOD AND APPARATUS, AND WORD SEARCH METHOD

CROSS-REFERENCE TO RELATED APPLICATIONS

This application claims the benefit under 35 USC § 119(a) of Korean Patent Application No. 10-2019-0127032, filed on Oct. 14, 2019, in the Korean Intellectual Property Office, the entire disclosure of which is incorporated herein by reference for all purposes.

BACKGROUND

1. Field

The following description relates to a word embedding and word search methods and apparatuses.

2. Description of Related Art

Much of knowledge has been published texts, like papers and books. Such accumulated knowledge is described in free text is a form that is understood by a user, and efforts are being made to extract structured knowledge from text using a natural language processing (NLP) technology.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a word embedding method including training a word embedding model based on characteristic information of a chemical substance, and acquiring an embedding vector of a word representing the chemical substance from the word embedding model, wherein the word embedding model is configured to predict a context word of an input word.

The training of the word embedding model may include training the word embedding model based on any one or any combination of structure information, composition information, and physical property information of the chemical substance.

The training of the word embedding model may include training the word embedding model to output a context word of the word representing the chemical substance, in response to an input of structure information of the chemical substance to the word embedding model.

The structure information of the chemical substance may be determined based on a format of one of a fingerprint, a simplified molecular-input line-entry system (SMILES), a graph, or an image.

The training of the word embedding model may include training the word embedding model to output a context word of the word representing the chemical substance is output from the word embedding model, in response to an input of composition information of the chemical substance to the word embedding model.

The composition information of the chemical substance may be acquired from the word representing the chemical substance.

The word representing the chemical substance may be split into letters or elements and the letters or elements are sequentially input to the word embedding model.

The training of the word embedding model may include training the word embedding model to output physical property information of the chemical substance from the word embedding model.

The physical property information may include information about any one or any combination of a mass, a volume, a color, a melting point, and a boiling point of the chemical substance.

The word embedding method may include inputting the embedding vector to a portion corresponding to the word representing the chemical substance in a word embedding matrix corresponding to the word embedding model.

The word embedding method may include determining whether a word with an embedding vector to be generated represents a chemical material.

In another general aspect, there is provided another word search method including receiving characteristic information of a chemical substance or a word representing the chemical substance, and outputting a word representing a substance having a characteristic similar to the chemical substance based on a word embedding matrix, wherein the word embedding matrix is acquired from a word embedding model trained based on characteristic information of a plurality of chemical substances, and the word embedding model is configured to predict a context word of an input word.

The characteristic information of the chemical substance may include any one or any combination of structure information, composition information, and physical property information of the chemical substance.

In another general aspect, there is provided a word embedding apparatus including a processor configured to train a word embedding model based on characteristic information of a chemical substance, and acquire an embedding vector of a word representing the chemical substance from the word embedding model, and the word embedding model is configured to predict a context word of an input word.

The processor may be configured to train the word embedding model based on any one or any combination of structure information, composition information, and physical property information of the chemical substance.

The processor may be configured to train the word embedding model to output a context word of the word representing the chemical substance, in response to an input of structure information of the chemical substance to the word embedding model.

The processor may be configured to train the word embedding model to output a context word of the word representing the chemical substance, in response to an input of composition information of the chemical substance to the word embedding model.

The processor may be configured to train the word embedding model to output physical property information of the chemical substance.

The processor may be configured to input the embedding vector to a portion corresponding to the word representing the chemical substance in a word embedding matrix corresponding to the word embedding model.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The following structural or functional descriptions of examples disclosed in the present disclosure are merely intended for the purpose of describing the examples and the examples may be implemented in various forms. The examples are not meant to be limited, but it is intended that various modifications, equivalents, and alternatives are also covered within the scope of the claims.

Although terms of "first" or "second" are used to explain various components, the components are not limited to the terms. These terms should be used only to distinguish one component from another component. For example, a "first" component may be referred to as a "second" component, or similarly, and the "second" component may be referred to as the "first" component within the scope of the right according to the concept of the present disclosure.

It will be understood that when a component is referred to as being "connected to" another component, the component can be directly connected or coupled to the other component or intervening components may be present.

As used herein, the singular forms are intended to include the plural forms as well, unless the context clearly indicates otherwise. It should be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Hereinafter, examples will be described in detail with reference to the accompanying drawings, and like reference numerals in the drawings refer to like elements throughout.

Figure 1:
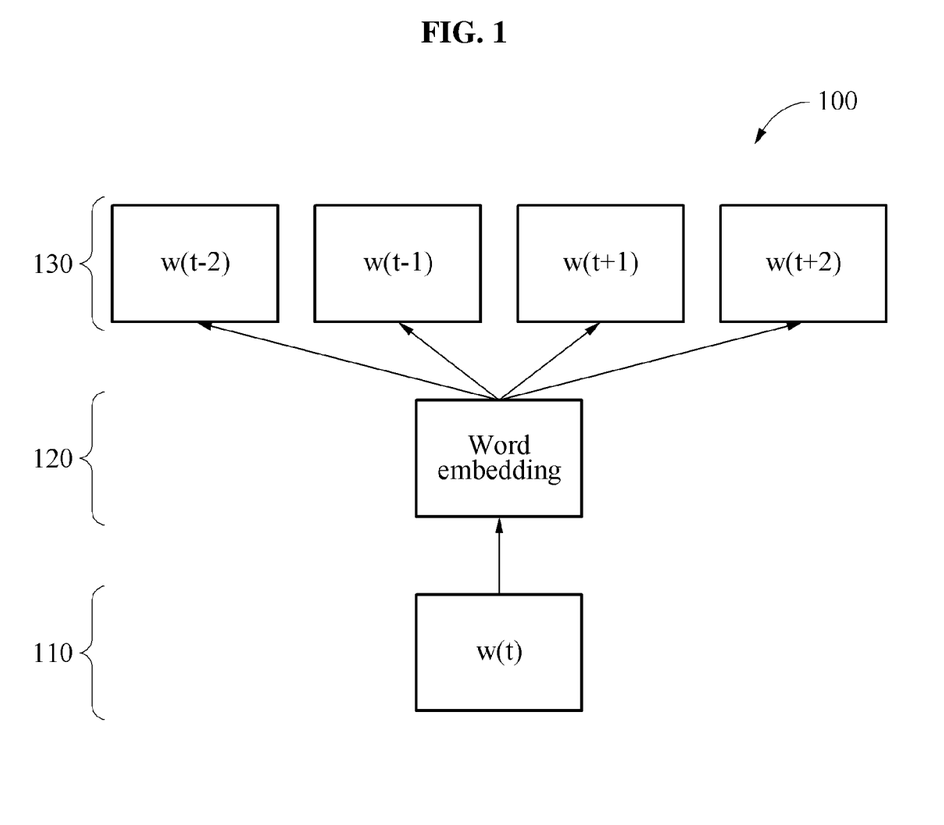
FIG. 1 illustrates an example of a word embedding model.

FIG. 1 illustrates an example of a word embedding model 100.

Referring to FIG. 1, the word embedding model 100 includes an input layer 110, a hidden layer 120 and an output layer 130.

The word embedding model 100 is a model used to express a word in a form of a vector, and may be a neural network based on Word2Vec that finds hidden knowledge in text in an unsupervised form even though a domain knowledge does not exist. The Word2Vec may be a scheme of obtaining a vector representation, or an embedding vector, of a word based on words appearing around related words based on a high possibility of the related words appearing in the same sentence. For example, when a word embedding model 100 that predicts words appearing around a word using the word as an input is trained, a hidden representation of the word embedding model 100 may be acquired as an embedding vector of the word. As described above, the word embedding model 100 may be referred to as Word2Vec for converting a word to a vector, and in particular, is also referred to as a "skip-gram model."

The word embedding model 100 is trained so that "n" words (for example, two words in FIG. 1) in each of a right side and a left side of a t-th word in a sentence are output from the output layer 130 in response to an input of the t-th word to the input layer 110, and an embedding vector of the t-th word is obtained in the hidden layer 120 of the trained word embedding model 100. Since words appearing around similar words are similar to each other, similar embedding vectors may be obtained. Also, the embedding vectors may include semantic information of corresponding words. Also, w(t) represents a one-hot vector that is a word identification (ID) representing the t-th word.

The t-th word input to the input layer 110 is referred to as a "target word", and the "n" words in each of the right side and the left side of the t-th word output from the output layer 130 are referred to as "context words". Also, the hidden layer 120 includes at least one layer, and is referred to as a "projection layer.

For example, when the target word is a word representing a chemical substance, the word embedding model 100 may be trained based on a characteristic of the chemical substance, to determine an embedding vector so that the characteristic of the chemical substance is reflected, which will be further described below.

In an example, the word embedding model 100 may be implemented as an artificial neural network including a two-dimensional convolutional neural network (CNN) and a pretrained spatial pyramid pooling network. In an example, the CNN may be a deep neural network (DNN). In an example, the DNN may include a region proposal network (RPN), a classification network, a reinforcement learning network, a fully-connected network (FCN), a deep convolutional network (DCN), a long-short term memory (LSTM) network, and a grated recurrent units (GRUs). In an example, the CNN includes a plurality of layers, each including a plurality of nodes. Also, the CNN includes connection weights that connect the plurality of nodes included in each of the plurality of layers to a node included in another layer of the CNN.

In an example, the CNN may receive a target word. In such an example, a convolution operation is performed on the target word with a kernel, and as a result, the feature maps are output. The convolution operation is performed again on the output feature maps as input feature maps, with a kernel, and new feature maps are output. When the convolution operation is repeatedly performed as such, a recognition result with respect to features of the target word may be finally output through the output layer of the CNN.

Figure 2:
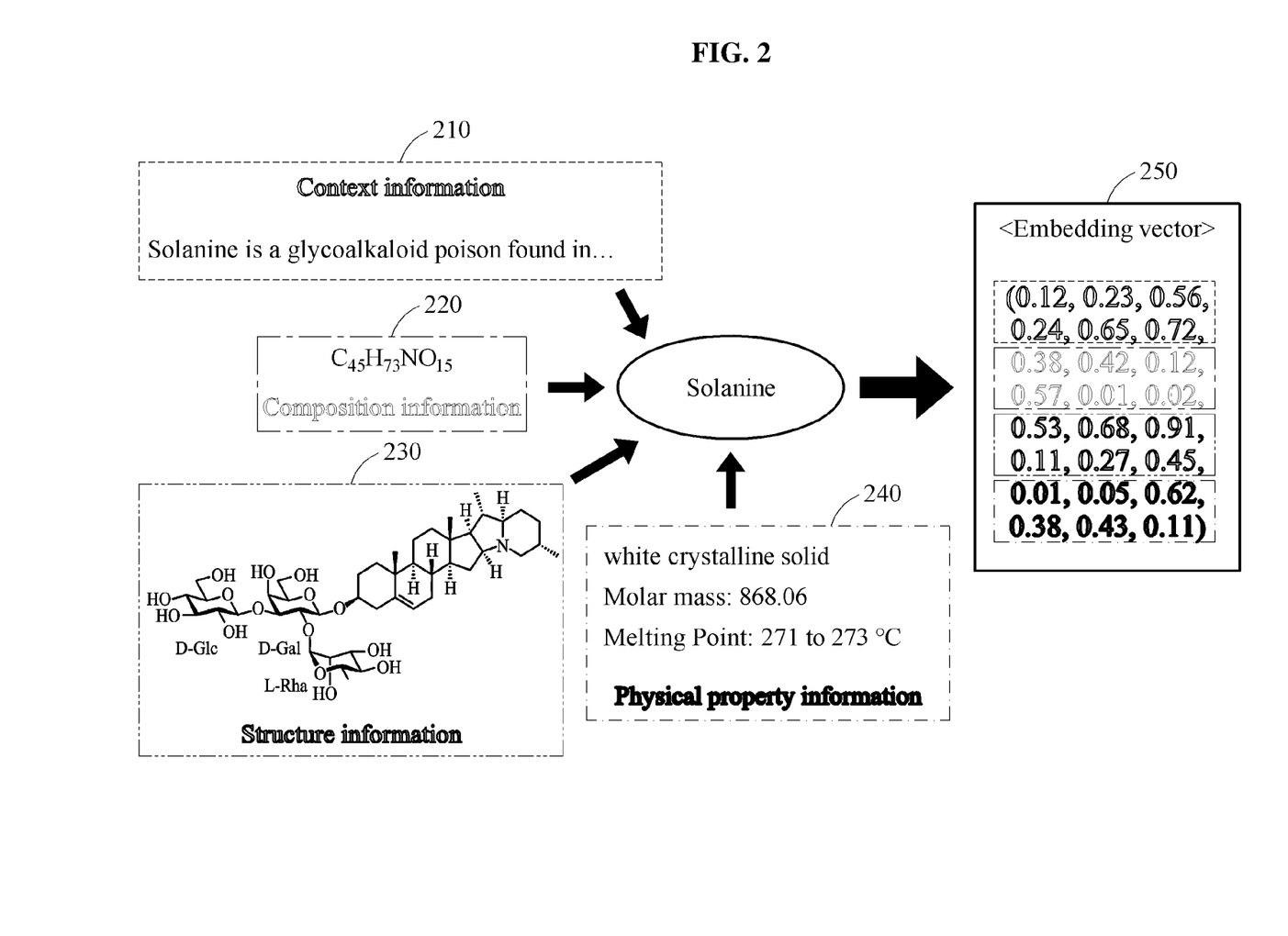
FIG. 2 illustrates an example of a process of generating an embedding vector.

FIG. 2 illustrates an example of a process of generating an embedding vector.

FIG. 2 illustrates various elements that may be used to determine an embedding vector 250.

When a general word is not related to a chemical substance, context information 210 shown in literature may be used to determine the embedding vector 250. For example, the embedding vector 250 may be determined using a word embedding model that is trained based on a target word and context words.

For example, when a word represents a chemical substance, the embedding vector 250 may be determined based on a characteristic of the chemical substance. In this example, the characteristic of the chemical substance includes composition information 220, structure information 230, and physical property information 240. The composition information 220 is contained in a chemical substance word, and thus lexical information is encoded and used as the composition information 220. The structure information 230 indicates a chemical structure or a molecular structure of the chemical substance, and may be determined based on any one of a format of one of a fingerprint, a simplified molecular-input line-entry system (SMILES), a graph, and an image. The physical property information 240 includes information about any one or any combination of a mass, a volume, a color, a melting point, and a boiling point of the chemical substance. The embedding vector 250 of FIG. 2 may be determined by reflecting any one or any combination of the context information 210, the composition information 220, the structure information 230, and the physical property information 240, which are described above. Also, context words or physical properties of chemical substance words with similar characteristics are also similar to each other, and thus similar embedding vectors may be obtained and chemical substances with similar characteristics may be retrieved based on a cosine similarity between embedding vectors. When embedding vectors are represented in a two-dimensional (2D) plane, embedding vectors of chemical substance words with similar characteristics may be located adjacent to each other.

Figure 3:
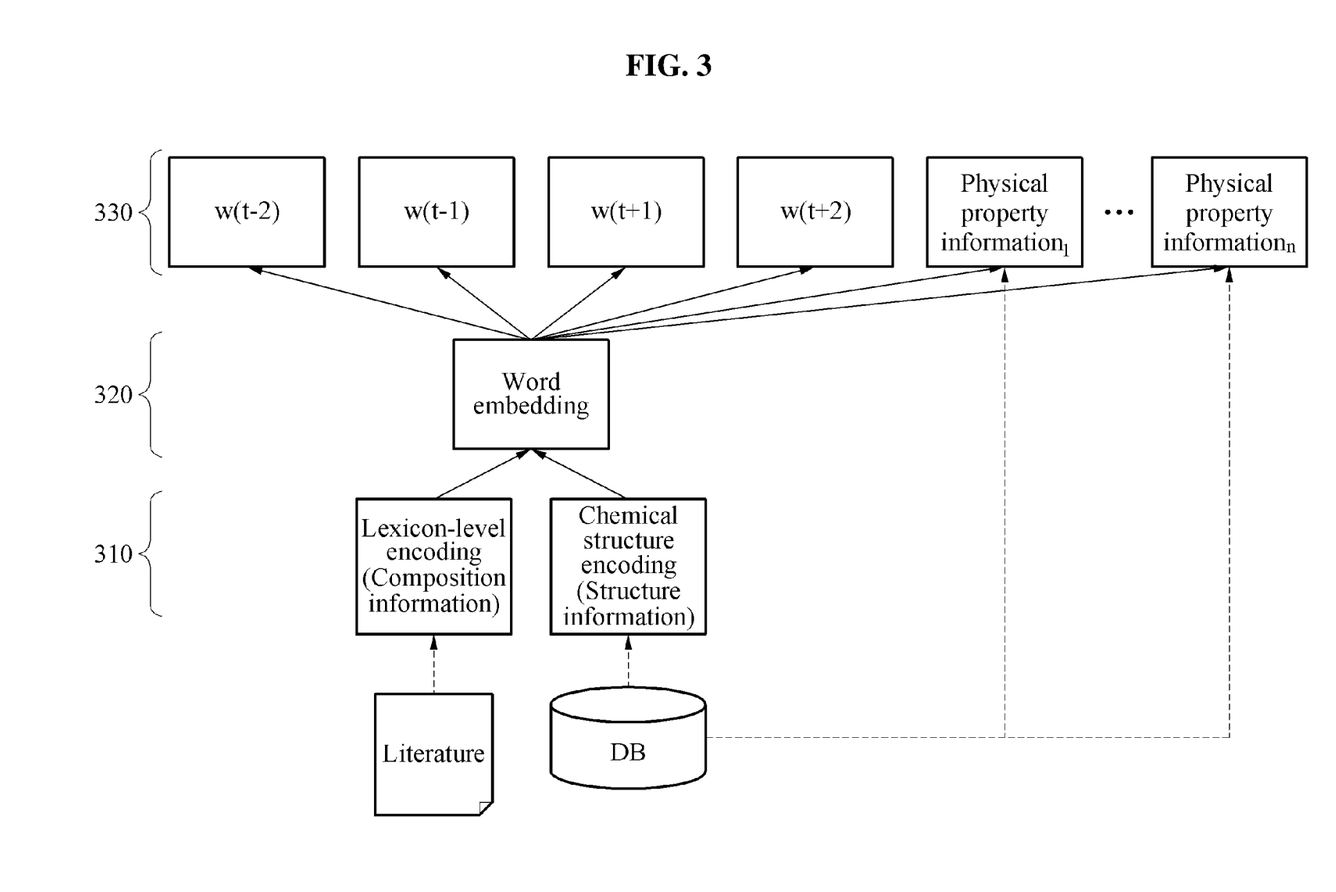
FIG. 3 illustrates an example of a process of training a word embedding model.

FIG. 3 illustrates an example of a process of training a word embedding model.

FIG. 3 illustrates a word embedding model used to determine an embedding vector of a word representing a chemical substance. A word appearing in literature may be, for example, a general word that is not related to a chemical substance, or a word representing a chemical substance. In an example, whether a word is a word representing a chemical substance may be determined by a chemical entity recognizer. For example, when a word to be modeled represents a chemical substance, an embedding vector may be acquired by operations that will be described below.

As described above, composition information is contained in a word representing a chemical substance. When a word representing a chemical substance is extracted from literature, composition information may be acquired by performing a lexicon-level encoding. The acquired composition information is input an input layer 310.

Also, structure information of the chemical substance determined through a chemical structure encoding may be acquired from a database (DB). The acquired structure information may be input to the input layer 310.

For the word representing the chemical substance, the composition information and/or the structure information of the chemical substance may be input to the input layer 310 of the word embedding model. A word ID indicating the word may not be input to the input layer 310.

Also, physical property information of the chemical substance may be acquired from the DB. The word embedding model may be trained so that the acquired physical property information may be output from an output layer 330.

In an example, the word embedding model may be trained to output a context word of the word representing the chemical substance, in response to the composition information and/or the structure information of the chemical substance being input to the word embedding model. In another example, the word embedding model may be trained to output a context word of the word representing the chemical substance and the physical property information of the chemical substance, in response to the composition information and/or the structure information of the chemical substance being input to the word embedding model. The word embedding model may enable prediction of the physical property information of the chemical substance as well as the context word, and may also be trained through multi-task learning.

As described above, training may be performed using the composition information and structure information that are inherent characteristics of the chemical substance as training input data of the word embedding model, and using the physical property information as training output data, and thus it is possible to acquire an embedding vector reflecting any one or any combination of the composition information, the structure information and the physical property information of the chemical substance.

Figure 4:
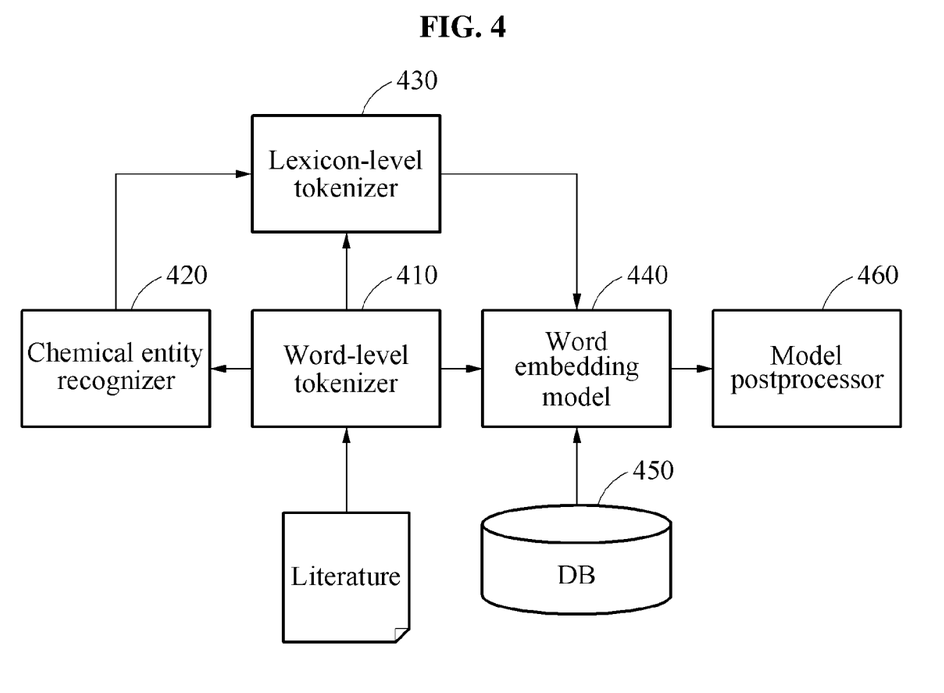
FIGS. 4 and 5 illustrate examples of an operation of a word embedding apparatus.
Figure 5:
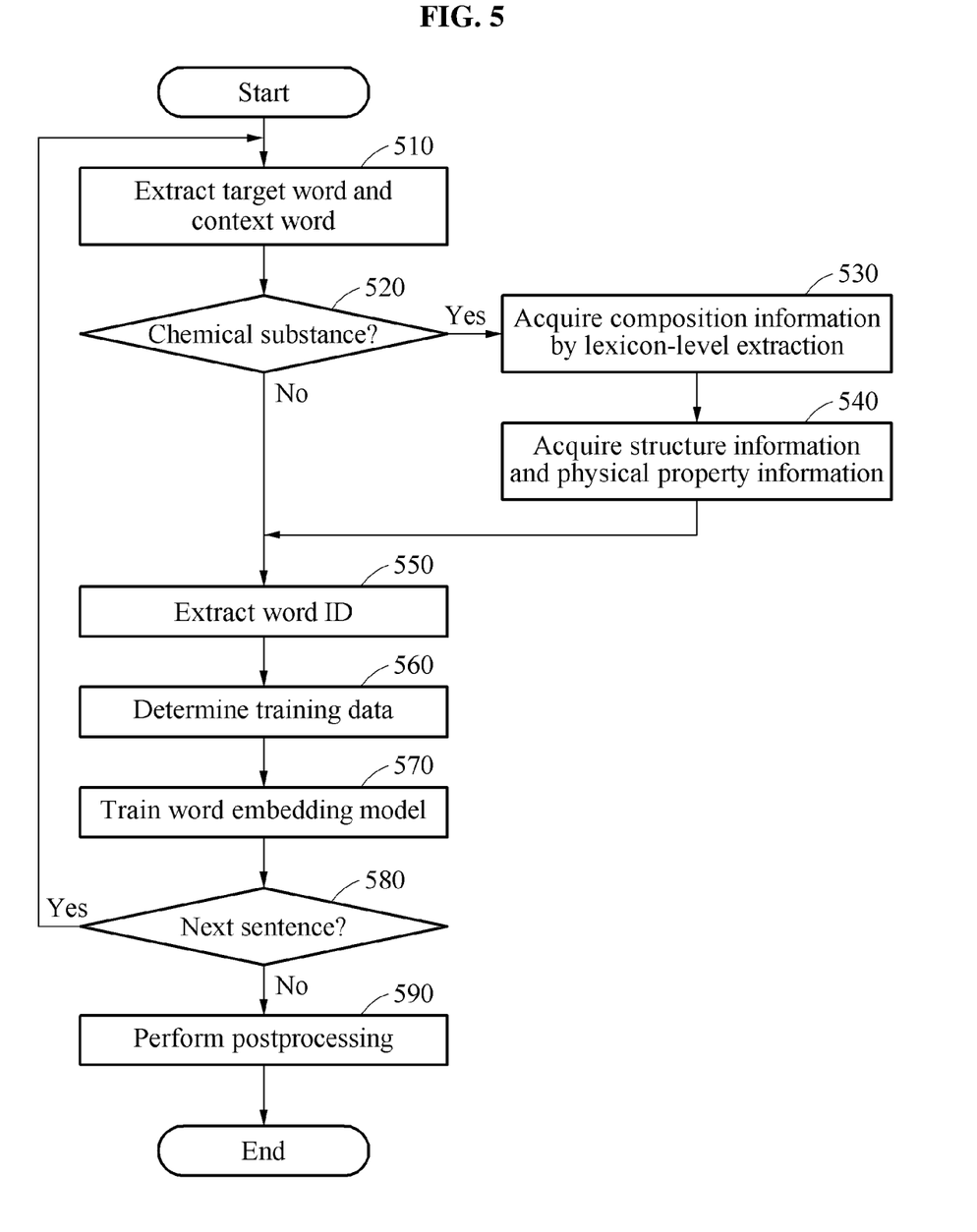

FIGS. 4 and 5 illustrate examples of an operation of a word embedding apparatus.

FIG. 4 is a diagram illustrating an example of an operation of a word embedding apparatus. A word-level tokenizer 410 splits a sentence appearing in literature into words. A chemical entity recognizer 420 determines whether a word with an embedding vector to be generated represents a chemical substance. A lexicon-level tokenizer 430 splits a word into lexical items smaller than a word. For example, the lexicon-level tokenizer 430 may split a word on a letter basis or an element basis. In an example, a word "$CuGaTe_2$" may be split into letters "C", "u", "G", "a", "T", "e" and "2", or into elements "Cu", "Ga", "Te" and "2". The letters or elements may be sequentially input to a word embedding model 440. The word embedding model 440 is a model that is to be finally trained, and a DB 450 stores structure information and physical property information of a chemical substance. Depending on circumstances, the DB 450 may be located outside the word embedding apparatus and may be connected to the word embedding apparatus via a wired and/or wireless network, or may be included in the word embedding apparatus. A model postprocessor 460 postmodifies the trained word embedding model 440. Since embedding vectors are acquired for each word ID of general words that are not related to a chemical substance, but a word ID of a word representing a chemical substance is not used in training, a postprocessing process may be performed. The postprocessing process will be further described below with reference to FIG. 6.

FIG. 5 is a diagram illustrating an example of an operation of a word embedding apparatus. The operations in FIG. 5 may be performed in the sequence and manner as shown, although the order of some operations may be changed or some of the operations omitted without departing from the spirit and scope of the illustrative examples described. Many of the operations shown in FIG. 5 may be performed in parallel or concurrently. One or more blocks of FIG. 5, and combinations of the blocks, can be implemented by special purpose hardware-based computer, and devices such as a processor, that perform the specified functions, or combinations of special purpose hardware and computer instructions. In addition to the description of FIG. 5 below, the descriptions of FIGS. 1-4 is also applicable to FIG. 5 and are incorporated herein by reference. Thus, the above description may not be repeated here.

In operation 510, the word embedding apparatus extracts a target word with an embedding vector to be generated, and a context word from literature. In operation 520, the word embedding apparatus determines whether the target word represents a chemical substance. In an example, when the target word is a general word that is not related to the chemical substance, operation 550 may be performed. In another example, when the target word represents the chemical substance, operation 530 may be performed. In operation 530, the word embedding apparatus acquires composition information of the chemical substance by splitting the target word into lexical items. In operation 540, the word embedding apparatus acquires structure information and physical property information of the chemical substance from a DB. In operation 550, the word embedding apparatus extracts a word ID of the target word and/or the context word.

In operation 560, the word embedding apparatus determines training data based on any one or any combination of the composition information, the structure information, the physical property information, and the word ID of the target word and/or the context word. The composition information, the structure information and the word ID of the target word may be determined as training input data, and the physical property information and the word ID of the context word may be determined as training output data. In operation 570, the word embedding apparatus trains a word embedding model based on the determined training data. In operation 580, the word embedding apparatus determines whether a next sentence exists in the literature. In an example, when the next sentence exists in the literature, operation 510 may be performed on the next sentence. In another example, when the next sentence does not exist in the literature, operation 590 may be performed. In operation 590, the word embedding apparatus performs a postprocessing on the word embedding model. An example of the postprocessing will be described below with reference to FIG. 6.

Figure 6:
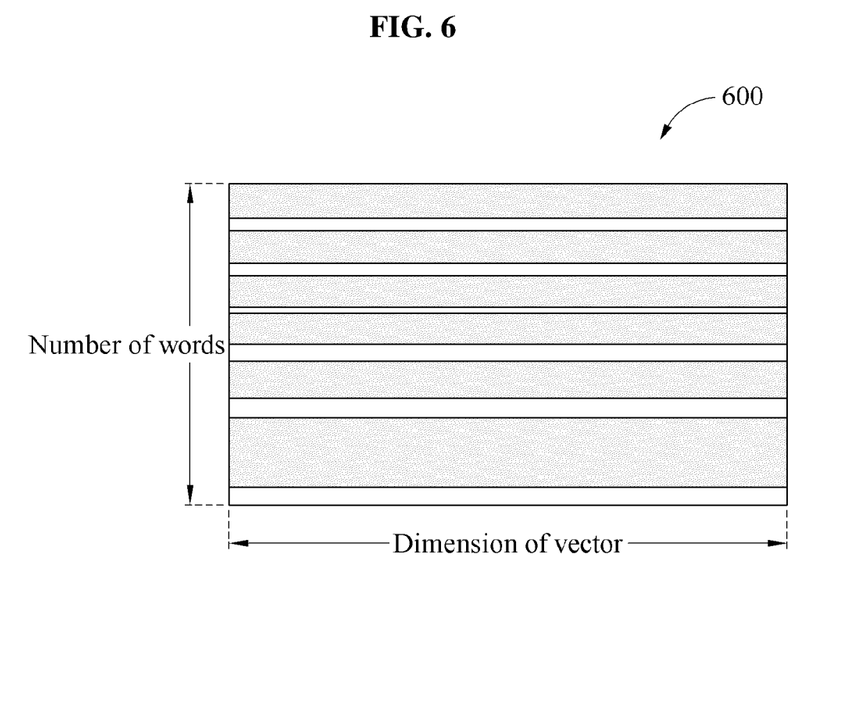
FIG. 6 illustrates an example of a process of performing a postprocessing on a word embedding matrix.

FIG. 6 illustrates an example of performing postprocessing on a word embedding matrix.

FIG. 6 illustrates an m×n word embedding matrix 600. In the word embedding matrix 600, an axis represents "m" words, and another axis represents an "n" dimension of a vector. Each row of the word embedding matrix 600 represents an embedding vector of one word, and may correspond to a word ID of a corresponding word. An n-dimension embedding vector is determined for each word ID. Since a word ID of a word representing a chemical substance is not input to a word embedding model during training, an embedding vector is not input to a row corresponding to the word ID merely by training the word embedding model. In the word embedding matrix 600 of FIG. 6, a white portion indicates a row to which an embedding vector is not input.

Thus, through a postprocessing, an embedding vector of a chemical substance word acquired during training may be input to a portion corresponding to the chemical substance word in the word embedding matrix 600. By performing the above postprocessing process, the word embedding matrix 600 without an empty portion may be completed.

Figure 7:
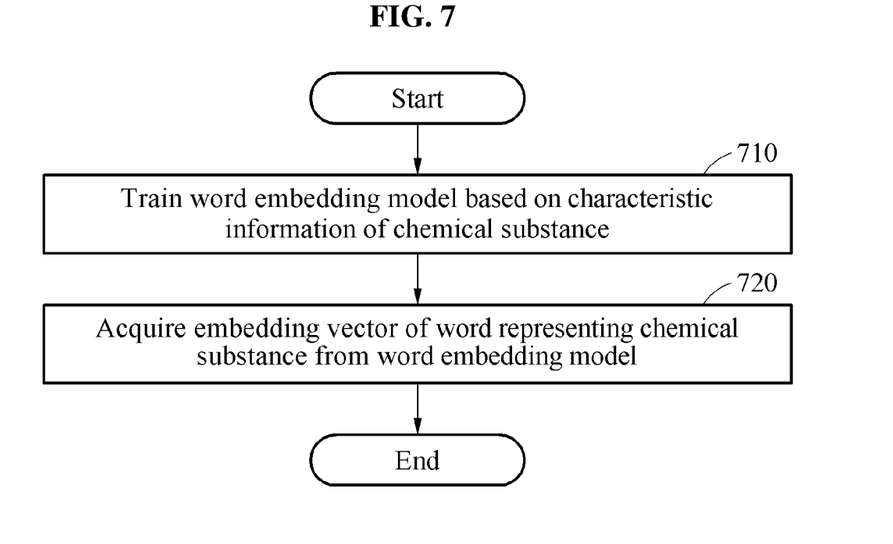
FIG. 7 illustrates an example of a word embedding method.

FIG. 7 illustrates an example of a word embedding method. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently. One or more blocks of FIG. 7, and combinations of the blocks, can be implemented by special purpose hardware-based computer, and devices such as a processor, that perform the specified functions, or combinations of special purpose hardware and computer instructions. In addition to the description of FIG. 7 below, the descriptions of FIGS. 1-6 is also applicable to FIG. 7 and are incorporated herein by reference. Thus, the above description may not be repeated here.

The word embedding method of FIG. 7 is performed by, for example, a processor of a word embedding apparatus.

In operation 710, the word embedding apparatus trains a word embedding model based on characteristic information of a chemical substance. The word embedding model predicts a context word of an input word.

The word embedding apparatus trains the word embedding model based on any one or any combination of structure information, composition information and physical property information of a chemical substance. In an example, the word embedding apparatus may train the word embedding model so that a context word of a word representing the chemical substance may be output from the word embedding model in response to an input of the structure information of the chemical substance to the word embedding model. In another example, the word embedding apparatus may train the word embedding model so that a context word of a word representing the chemical substance may be output from the word embedding model in response to an input of the composition information of the chemical substance to the word embedding model. In another example, the word embedding apparatus may train the word embedding model so that the physical property information of the chemical substance may be output from the word embedding model.

In operation 720, the word embedding apparatus acquires an embedding vector of a word representing the chemical substance from the word embedding model.

Also, the word embedding apparatus inputs the embedding vector to a portion corresponding to the word representing the chemical substance in a word embedding matrix corresponding to the word embedding model.

In an example, prior to operation 710, the word embedding apparatus may determine whether a word with an embedding vector to be generated represents the chemical substance.

Figure 8:
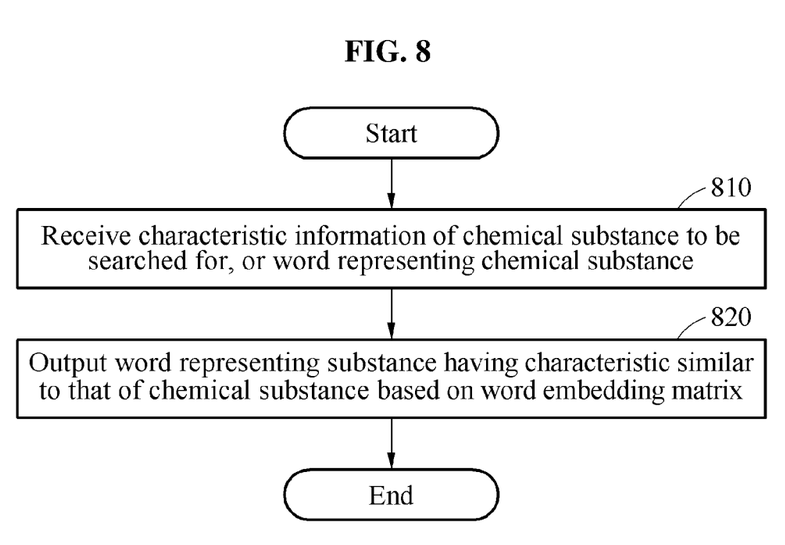
FIG. 8 illustrates an example of a word search method.

FIG. 8 illustrates an example of a word search method. The operations in FIG. 8 may be performed in the sequence and manner as shown, although the order of some operations may be changed or some of the operations omitted without departing from the spirit and scope of the illustrative examples described. Many of the operations shown in FIG. 8 may be performed in parallel or concurrently. One or more blocks of FIG. 8, and combinations of the blocks, can be implemented by special purpose hardware-based computer, and devices such as a processor, that perform the specified functions, or combinations of special purpose hardware and computer instructions. In addition to the description of FIG. 8 below, the descriptions of FIGS. 1-7 is also applicable to FIG. 8 and are incorporated herein by reference. Thus, the above description may not be repeated here.

The word search method of FIG. 8 is performed by, for example, a processor of a word search apparatus.

In operation 810, the word search apparatus receives characteristic information of a chemical substance that is to be searched for, or a word representing the chemical substance. The characteristic information of the chemical substance may include any one or any combination of structure information, composition information and physical property information of the chemical substance.

In operation 820, the word search apparatus outputs a word representing a substance having a characteristic similar to that of the chemical substance based on a word embedding matrix. The word embedding matrix may be acquired from a word embedding model that is trained based on characteristic information of a plurality of chemical substances. The word embedding model may predict a context word of an input word.

Figure 9:
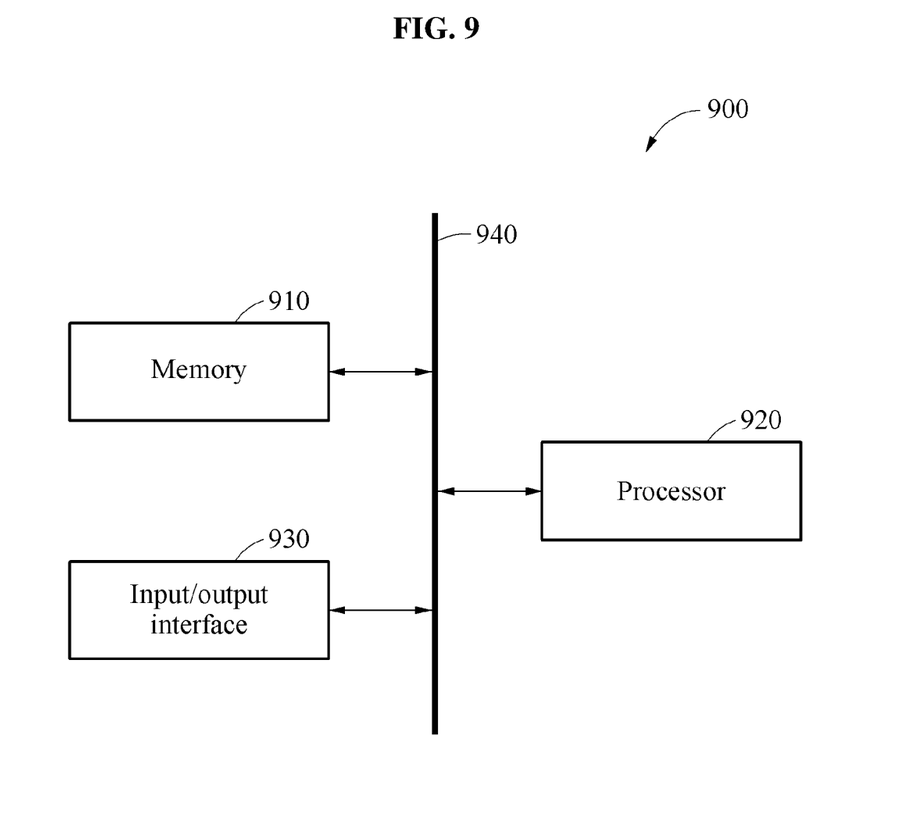
FIG. 9 illustrates an example of an electronic device.

FIG. 9 illustrates an example of an electronic device 900.

Referring to FIG. 9, the electronic device 900 includes a memory 910, a processor 920 and an input/output interface 930. The memory 910, the processor 920 and the input/output interface 930 communicate with each other via a bus 940.

In an example, the electronic device 900 may be, for example, a word embedding apparatus or a word search apparatus. In an example, the electronic device 900 may be implemented as various devices supporting word embedding or word search, such as, for example, a smart phone, a mobile telephone, a smartphone, a wearable smart device (such as, a ring, a watch, a pair of glasses, glasses-type device, a bracelet, an ankle bracket, a belt, a necklace, an earring, a headband, a helmet, a device embedded in the cloths, or an eye glass display (EGD)), a computing device, for example, a server, a laptop, a notebook, a subnotebook, a netbook, an ultra-mobile PC (UMPC), a tablet personal computer (tablet), a phablet, a mobile internet device (MID), a personal digital assistant (PDA), an enterprise digital assistant (EDA), an ultra mobile personal computer (UMPC), a portable lab-top PC, electronic product, for example, a robot, a digital camera, a digital video camera, a portable game console, an MP3 player, a portable/personal multimedia player (PMP), a handheld e-book, a global positioning system (GPS) navigation, a personal navigation device, portable navigation device (PND), a handheld game console, an e-book, a television (TV), a high definition television (HDTV), a smart TV, a smart appliance, a smart home device, or a security device for gate control, a walking assistance device, a smart speaker, a robot, various Internet of Things (IoT) devices, or a kiosk and may be performed by an application, middleware, or an operating system installed on a user device, or a program of a server interoperating with the corresponding application.

The memory 910 includes a computer-readable instruction. The processor 920 performs the above-described operations by executing an instruction stored in the memory 910. The memory 910 may include, for example, a volatile memory or a nonvolatile memory. The memory 910 includes a large capacity storage medium such as a hard disk to store the variety of data. Further details regarding the memory 910 is provided below.

The processor 920 is, for example, an apparatus configured to execute instructions or programs, or to control the electronic device 900. The processor 920 includes, for example, a central processing unit (CPU), a processor core, a multi-core processor, a reconfigurable processor, a multi-core processor, a multiprocessor, an application-specific integrated circuit (ASIC), and a field programmable gate array (FPGA), a graphics processing unit (GPU), or any other type of multi- or single-processor configuration. The electronic device 900 is connected to an external device via the input/output interface 930, and exchanges data. Further details regarding the processor 920 is provided below.

In an example, electronic device 900 interacts with the user through the input/output interface 930. In an example, the electronic device 900 displays a context word of an input word, the physical property information of the chemical substance, the structure information of the chemical substance, and a word representing a chemical substance on the input/output interface 930.

In an example, the input/output interface 930 may be a display that receives an input from a user or provides an output. In an example, the input/output interface 930 may function as an input device and receives an input from a user through a traditional input method, for example, a keyboard and a mouse, and a new input method, for example, a touch input, a voice input, and an image input. Thus, the input/output interface 930 may include, for example, a keyboard, a mouse, a touchscreen, a microphone, and other devices that may detect an input from a user and transmit the detected input to the data processing apparatus 800.

In an example, the input/output interface 930 may function as an output device, and provide an output of the electronic device 900 to a user through a visual, auditory, or tactile channel. The input/output interface 930 may include, for example, a display, a touchscreen, a speaker, a vibration generator, and other devices that may provide an output to a user.

However, the input/output interface 930 are not limited to the example described above, and any other displays, such as, for example, computer monitor and eye glass display (EGD) that are operatively connected to the electronic device 900 may be used without departing from the spirit and scope of the illustrative examples described. In an example, the input/output interface 930 is a physical structure that includes one or more hardware components that provide the ability to render a user interface, render a display, and/or receive user.

For example, both chemical substances "$LiMn_2O_2$" and "$LiNi_{0.5}Mn_{1.5}O_4$" contain lithium ions, and have similar structures. Embedding vectors of "$LiMn_2O_2$" and "$LiNi_{0.5}Mn_{1.5}O_4$" determined by the above-described method may reflect similar characteristics, and accordingly "$LiNi_{0.5}Mn_{1.5}O_4$" may be easily retrieved as a chemical substance similar to "$LiMn_2O_2$" using the embedding vectors. Thus, the word embedding apparatus and the word search apparatus may be utilized in a knowledge base construction, a reasoning and a knowledge discovery through a text analysis of a material field.

The electronic device 900 may process one or more of the operations described above.

The word embedding apparatus, word-level tokenizer 410, chemical entity recognizer 420, lexicon-level tokenizer 430, word embedding model 440, model postprocessor 460 post-modifies the trained word embedding model 440, and other apparatuses, units, modules, devices, and other components are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In an example, the instructions or software includes at least one of an applet, a dynamic link library (DLL), middleware, firmware, a device driver, an application program storing the word embedding method. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, card type memory such as multimedia card, secure digital (SD) card, or extreme digital (XD) card, magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A word embedding method comprising:
   training a word embedding model based on characteristic information of a chemical substance to output a context word of a word representing the chemical substance, in response to an input of composition information of the chemical substance; and
   acquiring an embedding vector of the word representing the chemical substance from the word embedding model,
   wherein the word representing the chemical substance is split into letters or elements and the letters or the elements are sequentially input to the word embedding model.

2. The word embedding method of claim 1, wherein the training of the word embedding model comprises training the word embedding model based on any one or any combination of structure information, composition information, and physical property information of the chemical substance.

3. The word embedding method of claim 1, wherein the training of the word embedding model further comprises training the word embedding model to output a context word of the word representing the chemical substance, in response to an input of structure information of the chemical substance to the word embedding model.

4. The word embedding method of claim 3, wherein the structure information of the chemical substance is determined based on a format of one of a fingerprint, a simplified molecular-input line-entry system (SMILES), a graph, or an image.

5. The word embedding method of claim 1, wherein the composition information of the chemical substance is acquired from the word representing the chemical substance.

6. The word embedding method of claim 1, wherein the training of the word embedding model further comprises training the word embedding model to output physical property information of the chemical substance from the word embedding model.

7. The word embedding method of claim 6, wherein the physical property information comprises information about any one or any combination of a mass, a volume, a color, a melting point, and a boiling point of the chemical substance.

8. The word embedding method of claim 1, further comprising:
   inputting the embedding vector to a portion corresponding to the word representing the chemical substance in a word embedding matrix corresponding to the word embedding model.

9. The word embedding method of claim 1, further comprising:
   determining whether a word with an embedding vector to be generated represents a chemical material.

10. A non-transitory computer-readable storage medium storing instructions that, when executed by a processor, cause the processor to perform the method of claim 1.

11. A word search method comprising:
    receiving characteristic information of a chemical substance or a word representing the chemical substance; and
    outputting a word representing a substance having a characteristic similar to the chemical substance based on a word embedding matrix,
    wherein the word embedding matrix is acquired from a word embedding model trained based on characteristic information of a plurality of chemical substances to output a context word of a word representing the chemical substance, in response to an input of composition information of the chemical substance, and
    wherein the word representing the chemical substance is split into letters or elements and the letters or the elements are sequentially input to the word embedding model is configured to predict a context word of an input word.

12. The word search method of claim 11, wherein the characteristic information of the chemical substance comprises any one or any combination of structure information, composition information, and physical property information of the chemical substance.

13. The word embedding apparatus comprising:
    a processor configured to:
    train a word embedding model to output physical property information of a chemical substance based on characteristic information of the chemical substance; and
    acquire an embedding vector of a word representing the chemical substance from the word embedding model, and
    the word embedding model is configured to predict a context word of an input word,
    wherein the physical property information comprises information about any one or any combination of a mass, a volume, a color, a melting point, and a boiling point of the chemical substance.

14. The word embedding apparatus of claim 13, wherein the processor is further configured to train the word embedding model based on any one or any combination of structure information, composition information, and the physical property information of the chemical substance.

15. The word embedding apparatus of claim 13, wherein the processor is further configured to train the word embedding model to output a context word of the word representing the chemical substance, in response to an input of structure information of the chemical substance to the word embedding model.

16. The word embedding apparatus of claim 13, wherein the processor is further configured to train the word embedding model to output a context word of the word representing the chemical substance, in response to an input of composition information of the chemical substance to the word embedding model.

17. The word embedding apparatus of claim 13, wherein the processor is further configured to input the embedding vector to a portion corresponding to the word representing the chemical substance in a word embedding matrix corresponding to the word embedding model.

* * * * *